(12) United States Patent
Kudo et al.

(10) Patent No.: US 7,994,342 B2
(45) Date of Patent: Aug. 9, 2011

(54) METHOD FOR PRODUCING OPTICALLY ACTIVE SUCCINIMIDE COMPOUND

(75) Inventors: Yoshihiro Kudo, Funabashi (JP); Osamu Yamada, Funabashi (JP)

(73) Assignees: Nissan Chemical Industries, Ltd., Tokyo (JP); Dainippon Sumitomo Pharma Co., Ltd., Osaka (JP)

( * ) Notice: Subject to any disclaimer, the term of this patent is extended or adjusted under 35 U.S.C. 154(b) by 218 days.

(21) Appl. No.: 12/311,048

(22) PCT Filed: Sep. 20, 2007

(86) PCT No.: PCT/JP2007/068267
§ 371 (c)(1),
(2), (4) Date: Mar. 18, 2009

(87) PCT Pub. No.: WO2008/035735
PCT Pub. Date: Mar. 27, 2008

(65) Prior Publication Data
US 2010/0003729 A1    Jan. 7, 2010

(30) Foreign Application Priority Data
Sep. 20, 2006   (JP) .................................. 2006-254446

(51) Int. Cl.
C07D 207/00   (2006.01)
C07D 295/00   (2006.01)

(52) U.S. Cl. ...................................................... 548/400

(58) Field of Classification Search .................. 548/400
See application file for complete search history.

(56) References Cited

FOREIGN PATENT DOCUMENTS

| JP | A-4-283562 | 10/1992 |
|----|-----------|---------|
| JP | A-5-186472 | 7/1993 |
| JP | A-6-192222 | 7/1994 |
| JP | A-2002-37771 | 2/2002 |
| JP | A-2002-47267 | 2/2002 |
| JP | A-2002-47268 | 2/2002 |

OTHER PUBLICATIONS

Negoro et al., J'nal of Med. Chem. vol. 41, Issue 21, p. 4118 et seq., (1998).*

Dernoncour et al., "Enantioselective Hydrolysis of 2-(Chlorophenoxy)Propionic Esters by Esterases," *Tetrahedron Letters*, 1987, pp. 4661-4664, vol. 28, No. 40, Pergamon Journals Ltd., Great Britain.

Klunder et al., "Enzymic Optical Resolution and Absolute Configuration of Tricyclo[5.2.1.0$^{2,6}$] Decadienones," *Tetrahedron Letters*, 1986, pp. 2543-2546, vol. 27, No. 22, Pergamon Journals Ltd., Great Britain.

Drueckhammer et al., "Chemoenzymic Synthesis of Chiral Furan Derivatives: Useful Building Blocks for Optically Active Structures," *J. Org. Chem.*, 1988, pp. 1607-1611, vol. 53, No. 8, American Chemical Society.

Negoro et al., "Novel, Highly Potent Aldose Reductase Inhibitors: (R)-(−)-2-(4-Bromo-2-fluorobenzyl)-1,2,3,4-tetrahydropyrrolo [1,2-a]pyrazine-4-spiro-3'-pyrrolidine-1,2',3,5'-tetrone (AS-3201) and Its Congeners," *J. Med. Chem.*, 1998, pp. 4118-4129, vol. 41, No. 21, American Chemical Society.

European Search Report mailed on Apr. 26, 2010 in corresponding European Patent Application No. 07 80 763.1.

* cited by examiner

*Primary Examiner* — Paul V. Ward
(74) *Attorney, Agent, or Firm* — Oliff & Berridge, PLC

(57) ABSTRACT

There is provided a novel method for producing an optically active succinimide compound which is a useful compound utilized as an intermediate raw material for pharmaceutical products or the like. The method for producing an optically active succinimide compound of formula (2) comprises processing a racemic compound of a succinimide compound of formula (1) in the presence of a hydrolase to selectively hydrolyze one of the enantiomers, and subjecting to a post-treatment.

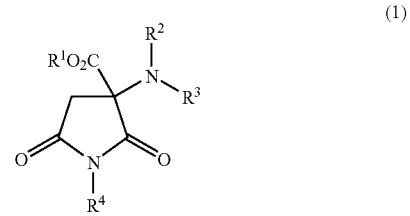

(1)

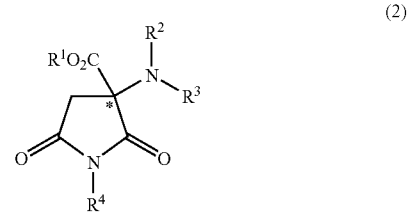

(2)

9 Claims, No Drawings

METHOD FOR PRODUCING OPTICALLY ACTIVE SUCCINIMIDE COMPOUND

TECHNICAL FIELD

The present invention relates to a novel method for producing an optically active succinimide compound which is excellent in the operability, is practicable with low cost and has high optical selectivity. In addition, a compound obtained according to the present invention is a useful compound utilized as an intermediate raw material for pharmaceutical products or the like.

BACKGROUND ART

A method for producing an optically active succinimide compound has been craved for and has been actively studied in the related art. As a method having general versatility, there is known a method in which a diastereomer salt of a racemic succinimide compound is produced using an optically active amine (such as cinchonidine) and is resolved by recrystallization (see Patent Document 1, Patent Document 2, Patent Document 3 and Patent Document 4). On the other hand, there are known some methods in which a racemic compound is hydrolyzed stereoselectively by an enzyme (see, for example, Non-patent Document 1, Non-patent Document 2 and Non-patent Document 3).

[Patent Document 1]
  Japanese Patent Application Publication No. JP-A-6-192222
[Patent Document 2]
  Japanese Patent Application Publication No. JP-A-2002-37771
[Patent Document 3]
  Japanese Patent Application Publication No. JP-A-200247267
[Patent Document 4]
  Japanese Patent Application Publication No. JP-A-2002-47268
[Non-patent Document 1]
  Tetrahedron Letters vol. 28, No 40, pp. 4661-4664 (1987)
[Non-patent Document 2]
  Tetrahedron Letters vol. 27, No. 22, pp. 2543-2546 (1986)
[Non-patent Document 3]
  Journal of Organic Chemistry vol. 53, No. 8, pp. 1607-1611 (1988)
[Non-patent Document 4]
  Journal of Medicinal Chemistry vol. 41, No. 21, pp. 4118-4129 (1998)

DISCLOSURE OF THE INVENTION

Problems to be Solved by the Invention

However, since the above methods have the following problems individually, the practice of a mass production by these methods is difficult.
(1) Cinchonidine is extremely expensive and the turn volume thereof is small, so that the supply thereof in a large amount is difficult.
(2) Cinchonidine is necessary in an amount of 1 mol or more relative to 1 mol of a substrate.
(3) Unless performing a plurality of recrystallizations, the optical purity is not enhanced.
(4) For obtaining an optically active compound from a racemic compound of a succinimide compound, there is required the operation in many steps such as forming a salt, recrystallization, removing an amine, and the like, so that the operation is extremely cumbersome.

Therefore, a novel production method which is excellent in the operability, is practicable with low cost and has high optical selectivity, which is impossible by a related-art method, has been expected.

Means for Solving the Problems

The present inventors have made extensive and intensive studies toward achieving the above problems and as a result, it is found that by using a hydrolysis reaction with an enzyme, the above problems can be achieved. Based on this novel finding, the present invention has been completed.

That is, the present invention relates to:
[1] A method for producing an optically active succinimide compound represented by formula (2):

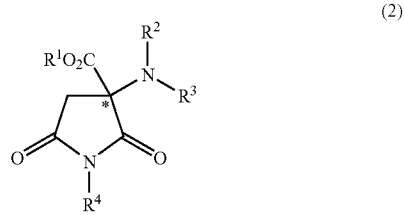

(where * represents; an asymmetric carbon atom; and $R^1$, $R^2$, $R^3$ and $R^4$ represent the same as defined in formula (1)), the method comprising: processing a racemic compound of a succinimide compound represented by the formula (1):

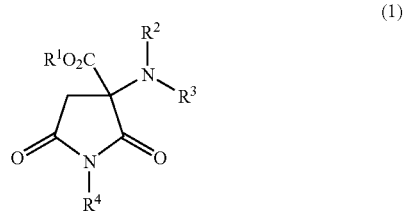

(where $R^1$ represents an alkyl group having 1 to 12 carbon atoms which may be a straight chain, branched or cyclic, or an aromatic group having 6 to 12 carbon atoms which may be substituted; $R^2$ and $R^3$ independently represent a hydrogen atom, an alkyl group having 1 to 12 carbon atoms which may be a straight chain, branched or cyclic, an acyl group having 2 to 6 carbon atoms which may be substituted, an alkoxycarbonyl group having 1 to 6 carbon atoms which may be substituted, a benzyl group of which an aromatic ring part may be substituted or a benzyloxycarbonyl group of which an aromatic ring part may be substituted, or $R^2$ and $R^3$ together with a nitrogen atom to which $R^2$ and $R^3$ are bonded can form a ring; and $R^4$ represents a hydrogen atom, an alkyl group having 1 to 12 carbon atoms which may be a straight chain, branched or cyclic, Or an aromatic group having 6 to 12 carbon atoms which may be substituted), in the presence of a hydrolase to selectively hydrolyze one of the enantiomers; and subjecting to a post-treatment.
[2] The production method according to [1], wherein the hydrolase is protease, esterase or lipase.
[3] The production method according to [1], wherein the hydrolase is lipase having an origin thereof in *Penicillium*, lipase having an origin thereof in *Candida antarctica* or esterase (PLE) derived from a pig liver.

[4] The production method according to [1], wherein the hydrolase is esterase (PLE) derived from a pig liver.

[5] The production method according to any one of [1] to [4], wherein the optically active succinimide compound represented by the formula (2) is a compound represented by formula (3):

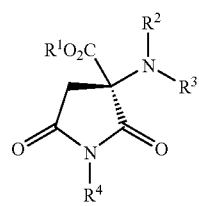

(where $R^1$, $R^2$, $R^3$ and $R^4$ represent the same as defined in the formula (1)).

[6] The production method according to any one of [1] to [4], wherein the optically active succinimide compound represented by the formula (2) is a compound represented by formula (4):

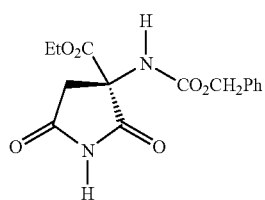

(where Et represents an ethyl group; and Ph represents a phenyl group).

[7] The production method according to [1], wherein the post-treatment is an extraction with an organic solvent.

[8] The production method according to any one of [1] to [4], wherein each of the optically active succinimide compounds represented by the formula (1) and the formula (2) is a compound in which $R^1$ represents an alkyl group having 1 to 6 carbon atoms which may be a straight chain or branched; $R^2$ represents a benzyloxycarbonyl group of which an aromatic ring part may be substituted, and $R^3$ and $R^4$ represent a hydrogen atom.

[9] A production method of (R)-(−)-2-(4-bromo-2-fluorobenzyl)-1,2,3,4-tetrahydropyrrolo[1,2-a]pyrazin-4-spiro-3'-pyrrolidine-1,2',3,5'-tetraone (hereinafter, referred to as "compound A") comprising: converting an optically active succinimide compound produced by the production method as described in [6] or [8] to the compound A.

[10] A production method of the compound A comprising:
(a) producing an optically active succinimide compound by the production method as described in [6] or [8];
(b) converting a benzyloxycarbonylamino group of the optically active succinimide compound produced in the process (a) to an amino group;
(c) converting an amino group or the product obtained in the process (b) to a pyrrole-1-yl group;
(d) converting a pyrrole-1-yl group of the product obtained in the process (c) to a 2-trichloroacetylpyrrole-1-yl group; and
(e) reacting the product obtained in the process (d) with 4-bromo-2-fluorobenzylamine to convert to the compound A.

Effects of the Invention

According to the production method of the present invention, an optically active succinimide compound useful as an intermediate raw material for pharmaceutical products or the like can be produced with low cost and simply.

BEST MODES FOR CARRYING OUT THE INVENTION

The definition of substituents of the present specification is shown as follows. Here, n—means normal, i—means iso, sec—means secondary and t—means tertiary.

The alkyl group having 1 to 12 carbon atoms which may be straight chain, branched or cyclic in the present specification represents a strait chain, branched or cyclic hydrocarbon group containing 1 to 12 carbon atoms and specific examples thereof include a methyl group, an ethyl group, an n-propyl group, an i-propyl group, a cyclopropyl group, an n-butyl group, an i-butyl group, a sec-butyl group, a t-butyl group, a cyclobutyl group, an n-pentyl group, a cyclopentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, an n-hexyl group, a cyclohexyl group, a 1-methylpentyl group, a 2-methylpentyl group, a 1,1-dimethylbutyl group, a 1,3-dimethylbutyl group, a heptyl group, a cycloheptyl group, an octyl group, a cyclooctyl group, a nonyl group, a decyl group, an undecyl group, a dodecyl group and an adamantyl group.

Examples of the aromatic group having 6 to 12 carbon atoms which may be substituted include a phenyl group and a naphthyl group which may be substituted with one or more substituent(s) the same as or different from each other which is/are selected from a halogen atom, an alkyl group having 1 to 12 carbon atoms, a cyano group, a nitro group, an alkylcarbonyl group having 1 to 12 carbon atoms, an alkyloxy group having 1 to 12 carbon atoms, di(alkyl having 1 to 12 carbon atoms) amino group, and the like.

Examples of the acyl group having 2 to 6 carbon atoms which may be substituted include a methylcarbonyl group, an ethylcarbonyl group, an n-propylcarbonyl group, an i-propylcarbonyl group, an n-butylcarbonyl group, an i-butylcarbonyl group, a sec-butylcarbonyl group, a 1-butylcarbonyl group and an n-pentylcarbonyl group which may be substituted with one or more substituent(s) the same as or different from each other which is/are selected from a fluorine atom, a chlorine atom, a bromine atom, an iodine atom, a nitro group, a cyano group, and the like.

Examples of the alkoxycarbonyl group having 1 to 6 carbon atoms which may be substituted include a methoxycarbonyl group, an ethoxycarbonyl group, an n-propyloxycarbonyl group, an i-propyloxycarbonyl group, an n-butyloxycarbonyl group, an i-butyloxycarbonyl group, a sec-butyloxycarbonyl group, a t-butyloxycarbonyl group, an n-pentyloxycarbonyl group and an n-hexyloxycarbonyl group which may be substituted with one or more substituent (s) the same as or different from each other which is/are selected from a fluorine atom, a chlorine atom, a bromine atom, an iodine atom, a nitro group, a cyano group, and the like.

Examples of the benzyl group of which the aromatic ring part may be substituted include a benzyl group of which an aromatic part may be substituted with one or more substituent (s) the same as or different from each other which is/are selected from a halogen atom, an alkyl group having 1 to 12 carbon atoms, a cyano group, a nitro group, an alkylcarbonyl group having 1 to 12 carbon atoms, an alkyloxy group having 1 to 12 carbon atoms, di(alkyl having 1 to 12 carbon atoms) amino group, and the like.

Examples of the benzyloxycarbonyl group of which the aromatic ring part may be substituted include a benzyloxycarbonyl group of which an aromatic part may be substituted with one or more substituent(s) the same as or different from each other which is/are selected from a halogen atom, an alkyl group having 1 to 12 carbon atoms, a cyano group, a nitro group, an alkylcarbonyl group having 1 to 12 carbon atoms, an alkyloxy group having 1 to 12 carbon atoms, di(alkyl having 1 to 12 carbon atoms) amino group, and the like.

The case in which "$R^2$ and $R^3$ are bonded to each other to form a ring" means a case in which $R^2$ and $R^3$ together with N, to which $R^2$ and $R^3$ are bonded, form a piperidine ring, a pyrrolidine ring, a succinimide ring, a maleimide ring, or the like.

Next, examples of the preferred substituent are as follows.

Examples of $R^1$ include a methyl group, an ethyl group, an n-propyl group, an i-propyl group, an n-butyl group, an i-butyl group, a sec-butyl group, a t-butyl group and a benzyl group.

Examples of $R^2$ include a hydrogen atom, a methyl group, an ethyl group and an n-propyl group.

Examples of $R^3$ include a benzyl group, a benzyloxycarbonyl group, an acetyl group and a t-butyloxycarbonyl group.

Examples of $R^4$ include a hydrogen atom, a methyl group, an ethyl group, an n-propyl group, an i-propyl group, an n-butyl group, an i-butyl group, a sec-butyl group, a t-butyl group and a benzyl group.

Hereinafter, the present invention will be described in more detail.

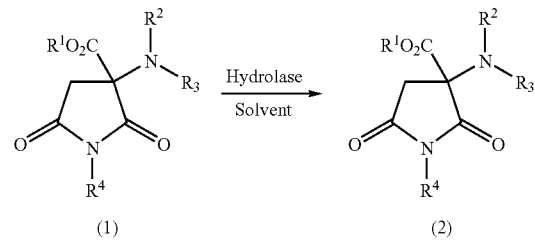

That is, in a solvent, when a hydrolase is added to a succinimide compound represented by the formula (1), one of the enantiomers only is selectively hydrolyzed and the optically active succinimide compound represented by the formula (2) can be produced.

Examples of the hydrolase to be used include protease, esterase and lipase, and the hydrolase is preferably lipase having an origin in *Penicillium* (for example Lipase R (manufactured by Amano Enzyme Inc.)), lipase having an origin in *Candida antarctica* (for example Chirazyme L-2 (manufactured by Roche Diagnostics CGmbH)), or esterase (PLE) derived from a pig liver (for example manufactured by Sigma-Aldrich Corporation, Roche Diagnostics GmbH, Bio-Catalytics, Inc.), more preferably esterase (PLE) extracted from a pig liver.

As the hydrolase, the enzyme of a natural-type or the enzyme which is commercially available as a processed product such as an immobilized product can be used and these enzymes can be used individually or in combination of two or more types thereof.

The amount used or the hydrolase can be used usually in a range of 0.01 to 3,000 mg, preferably in a range of 0.1 to 100 mg, relative to 1 g of a succinimide compound represented by the formula (1).

Examples of the solvent include water, a buffer solution solvent, an organic solvent, a mixed solvent of an organic solvent with water and a mixed solvent of an organic solvent with a buffer solution solvent.

As the buffer solution, the solution in which an acidic compound is mixed with an alkaline compound in water and pH of the resultant mixture is adjusted to an arbitrary value is used.

Examples of the acidic compound used in the buffer solution include phosphoric acid, citric acid, boric acid and acetic acid, and phosphoric acid and citric acid are preferably used.

Examples of the alkaline compound include sodium hydroxide, potassium hydroxide, lithium hydroxide and ammonia, and sodium hydroxide and potassium hydroxide are preferably used.

The buffer solution can be used in a pH range thereof of 3.0 to 10.0, preferably of 4.0 to 8.0.

The buffer solution can be used in a concentration range thereof of 0.01 to 2.0 mol/L, preferably of 0.03 to 0.3 mol/L.

The organic solvent is not particularly limited so long as it is stable under the present reaction condition and it does not hinder the objective reaction and examples thereof include alcohols (for example, ethanol, propanol, butanol, octanol, etc.), cellosolves (for example, methoxyethanol, ethoxyethanol, etc.), aprotic polar organic solvents (for example, dimethylformamide, dimethylsulfoxide, dimethylacetoamide, tetramethylurea, sulfolan, N-methylpyrrolidone, N,N-dimethylimidazolidinone, etc.), ethers (for example, diethyl ether, diisopropyl ether, t-butyl methyl ether, tetrahydrofuran, dioxane, etc.), aliphatic hydrocarbons (for example, pentane, hexane, c-hexane, octane, decane, decalin, petroleum ether, etc.), aromatic hydrocarbons (for example, benzene, chlorobenzene, o-dichlorobenzene, nitrobenzene, toluene, xylene, mesitylene, tetralin, etc.), halogenated hydrocarbons (for example, chloroform, dichloromethane, dichloroethane, carbon tetrachloride, etc.), ketones (for example, acetone, methyl ethyl ketone, methyl butyl ketone, methyl isobutyl ketone, etc.), lower aliphatic acid ester (for example, methyl acetate, ethyl acetate, butyl acetate, methyl propionate, etc.), alkoxy alkanes (for example, dimethoxyethane, diethoxyethane, etc.), and nitrites (for example, acetonitrile, propionitrile, butylonitrile, etc.), can be used.

The above organic solvents may be used individually or in combination of two or more types thereof.

The amount used of the solvent, which is usually in a range of 1 to 200 times, preferably 5 to 50 times, the mass of the succinimide compound represented by the formula (1), can be used.

The reaction temperature may be usually from 0° C. to the boiling point of a solvent to be used, preferably in a range of 0 to 80° C., more preferably in a range of 20 to 50° C.

As the reaction operation, corresponding to the change of pH of the reaction system, an acidic compound or an alkaline compound can be dropping-charged as, for example, an aqueous solution thereof to adjust the pH value of the reaction system to an arbitrary pH value.

The objective optically active succinimide compound represented by the formula (2) can be obtained for example, by filtering the reaction mixture to remove insoluble matters after the completion of the reaction; extracting the reactant with an appropriate solvent; washing the extracted product with water to remove hydrolyzed matters; and distilling off the solvent under reduced pressure to concentrate the objective product. In addition, if necessary, the objective product can be purified by recrystallization, distillation, silica gel column chromatography, and the like.

In addition, the compound represented by the formula (2) can be produced also by processing the compound represented by the formula (1) with microbes having a producing ability of a hydrolase, for example, cultures of such as *Penicillium* and *Candida antarctica* or processed matters thereof.

Further, Patent Document 1 indicates that the optically active succinimide compound represented by the formula (3) (where $R^1$ represents an alkyl group having 1 to 6 carbon atoms which may be a straight chain or branched; $R^2$ represents a benzyloxycarbonyl group of which an aromatic ring part may be substituted; and $R^3$ and $R^4$ represent a hydrogen atom) is useful as an intermediate of the compound A which is promising as a pharmaceutical product, and also describes a production method related thereto.

In addition, reference examples and examples of Patent Document 1 and experimental sections of Non-patent Document 4 specifically describe a method for producing the compound A from the optically active succinimide compound represented by the formula (4) and the production method consists of the following processes:
(i) converting a benzyloxycarbonylamino group of the optically active succinimide compound represented by the formula (4) to an amino group by hydrogenolyzing in ethanol using palladium carbon;
(ii) reacting the amino group of the product obtained in the process (i) with 2,5-dimethoxytetrahydrofuran in acetic acid;
(iii) reacting the product obtained in the process (ii) with trichloroacetyl chloride in chloroform;
(iv) reacting the product obtained in the process (iii) with a mixture of triethylamine and 4-bromo-2-fluorobenzylamine hydrochloride in dried dimethylformamide; and
(v) crystallizing and isolating the compound A obtained in the process (iv) from a mixed solvent of ethyl acetate and hexane.

EXAMPLES

Hereinafter, the present invention is described specifically referring to examples, however, which should not be construed as limiting the scope of the present invention.

Here, the optical purity of the optically active succinimide compound represented by the formula (2) was determined from the result of a measurement by a high performance liquid chromatography using an optically active column and from the area ratio with enantiomers.
Column: CHIRALPAK AD-H (manufactured by Daicel Chemical Industries, Ltd.)
Eluent: isopropyl alcohol/hexane=23/77 (in volume ratio)
Oven temperature: 40° C.
Detection method: UV 216 nm In addition, the quantitative yield of the optically active succinimide compound represented by the formula (2) was determined by performing a quantitative analysis using a reversed phase high performance liquid chromatography and using diallyl phthalate as an internal standard substance.
Column: XBridge C18 (manufactured by Waters Corporation)
Eluent: water/acetonitrile/acetic acid=58/4210.1 (in volume ratio)
Oven temperature: 40° C.
Detection method: UV 210 nm Example 1

Production of (R)-2-benzyloxycarbonylamino-2-ethoxycarbonyl succinimide 0.5 g of esterase (PLE (21 kU/g); manufactured by Sigma-Aldrich Corporation, lyophilized powder) were dissolved in 200 mL of 0.07 mol/L phosphate buffer solution of which pH value was adjusted to 6-5 and thereto, a solution in which 10 g of 2-benzyloxycarbonylamino-2-ethoxycarbonyl succinimide were dissolved in 20 g of tetrahydrofuran was added. The resultant mixture was stirred at 30° C. for 48 hours and thereto, 100 mL of t-butyl methyl ether were added. Thereafter, the resultant mixture was filtered with Celite (No. 545) and washed with 50 mL of t-butyl methyl ether. After the filtrate was removed, the organic phase was washed with 100 ml, of water several times and the solvent was distilled off under reduced pressure. Thereafter, the product was recrystallized in ethyl acetate and hexane to thereby obtaining 3.6 g (yield: 36%) of (R)-2-benzyloxycarbonylamino-2-ethoxycarbonyl succinimide having an optical purity of 98.9% e.e. (enantiomeric excess) as a white crystal.

Here, 2-benzyloxycarbonylamino-2-ethoxycarbonyl succinimide used in the present example was synthesized according to the method described in Japanese Patent Application Publication No. JP-A-5-186472.

Example 2

Production of (R)-2-benzyloxycarbonylamino-2-ethoxycarbonyl succinimide 5.0 g of 2-benzyloxycarbonylamino-2-ethoxycarbonyl succinimide were dissolved in 100 g of dimethylsulfoxide and thereto, 100 g of 0.05 mol/L citrate buffer solution (pH 4.4) were added, followed by adjusting pH value of the resultant mixture to 6.5 with a 5% sodium hydroxide aqueous solution. Thereto, 0.28 mL of esterase (PLE (2.7 kU/mL); manufactured by BioCatalytics, Inc., ammonium sulfate suspension) were added and the resultant mixture was stirred at 25° C. for 78 hours, followed by analyzing quantitatively the reaction mixture. As a result, in the reaction mixture, 2.4 g (quantitative yield: 48.6%) of (R)-2-benzyloxycarbonylamino-2-ethoxycarbonyl succinimide having an optical purity of 97-5% e.e. were contained

INDUSTRIAL APPLICABILITY

The production method of the present invention is to provide a novel production method of an optically active succinimide compound useful as an intermediate raw material for pharmaceutical products or the like.

The invention claimed is:
1. A method for producing an optically active succinimide compound represented by formula (2):

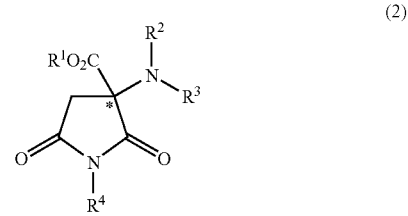

(where * represents an asymmetric carbon atom; and $R^1$, $R^2$, $R^3$ and $R^4$ represent the same as defined in formula (1)), the method comprising:
processing a racemic compound of a succinimide compound represented by the formula (1):

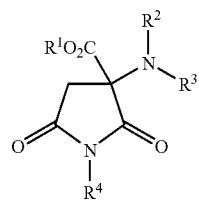

(1)

(where $R^1$ represents an alkyl group having 1 to 12 carbon atoms which may be a straight chain, branched or cyclic, or an aromatic group having 6 to 12 carbon atoms which may be substituted; $R^2$ and $R^3$ independently represent a hydrogen atom, an alkyl group having 1 to 12 carbon atoms which may be a straight chain, branched or cyclic, an acyl group having 2 to 6 carbon atoms which may be substituted, an alkoxycarbonyl group having 1 to 6 carbon atoms which may be substituted, a benzyl group of which an aromatic ring part may be substituted or a benzyloxycarbonyl group of which an aromatic ring part may be substituted, or $R^2$ and $R^3$ together with a nitrogen atom to which $R^2$ and $R^3$ are bonded can form a ring; and $R^4$ represents a hydrogen atom, an alkyl group having 1 to 12 carbon atoms which may be a straight chain, branched or cyclic, or an aromatic group having 6 to 12 carbon atoms which may be substituted), in the presence of a hydrolase to selectively hydrolyze one of the enantiomers; and subjecting to a post-treatment.

2. The method according to claim 1, wherein the hydrolase is protease, esterase or lipase.

3. The method according to claim 1, wherein the hydrolase is lipase having an origin thereof in *Penicillium*, lipase having an origin thereof in *Candida antarctica* or esterase (PLE) derived from a pig liver.

4. The method according to claim 1, wherein the hydrolase is esterase (PLE) derived from a pig liver.

5. The method according to claim 1, wherein the optically active succinimide compound represented by the formula (2) is a compound represented by formula (3):

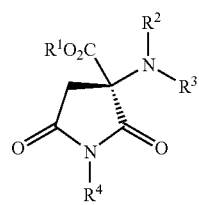

(3)

(where $R^1$, $R^2$, $R^3$ and $R^4$ represent the same as defined in the formula (1)).

6. The method according to claim 1, wherein the optically active succinimide compound represented by the formula (2) is a compound represented by formula (4):

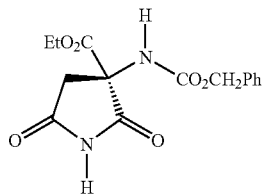

(4)

(where Et represents an ethyl group; and Ph represents a phenyl group).

7. The method according to claim 1, wherein the post-treatment is an extraction with an organic solvent.

8. The method according to claim 1, wherein each of the optically active succinimide compound represented by the formula (1) and the formula (2) is a compound in which $R^1$ represents an alkyl group having 1 to 6 carbon atoms which may be a straight chain or branched; $R^2$ represents a benzyloxycarbonyl group of which an aromatic ring part may be substituted; and $R^3$ and $R^4$ represent a hydrogen atom.

9. A method for producing (R)-(+2-(4-bromo-2-fluorobenzyl)-1,2,3,4-tetrahydropyrrolo[1,2-a]pyrazin-4-spiro-3'-pyrrolidine-1,2',3,5'-tetraone-comprising:

processing a racemic compound of a succinimide compound represented by the formula (1):

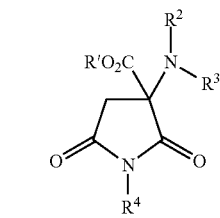

(1)

(where $R^1$ represents an ethyl group, $R^2$ represents a hydrogen atom, and $R^3$ represents benzyloxycarbonyl) in the presence of a hydrolase to selectively hydrolyze one of the enantiomers;

subjecting to a post-treatment to obtain a compound represented by formula (4):

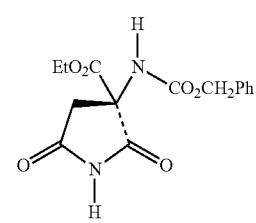

(4)

(where Et represents an ethyl group; and Ph represents a phenyl group); and converting the compound represented by formula (4) to (R)-(−)-2-(4-bromo-2-fluorobenzyl)-1,2,3,4-tetrahydropyrrolo[1,2-a]pyrazin-4-spiro-3'-pyrrolidine-1,2',3,5'-tetraone.

* * * * *